(12) United States Patent
Snyder

(10) Patent No.: US 12,226,588 B2
(45) Date of Patent: Feb. 18, 2025

(54) PROXIMALLY SEPERABLE CATHETERS AND ASSOCIATED METHODS

(71) Applicant: Bard Peripheral Vascular, Inc., Franklin Lakes, NJ (US)

(72) Inventor: Scott W. Snyder, Taylorsville, UT (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 763 days.

(21) Appl. No.: 17/481,066

(22) Filed: Sep. 21, 2021

(65) Prior Publication Data

US 2022/0105311 A1 Apr. 7, 2022

Related U.S. Application Data

(60) Provisional application No. 63/086,995, filed on Oct. 2, 2020.

(51) Int. Cl.
  *A61M 25/00* (2006.01)
  *A61L 29/04* (2006.01)
  *A61M 1/28* (2006.01)

(52) U.S. Cl.
  CPC ....... *A61M 25/0028* (2013.01); *A61L 29/042* (2013.01); *A61M 1/285* (2013.01); *A61M 2025/0034* (2013.01)

(58) Field of Classification Search
  None
  See application file for complete search history.

(56) References Cited

U.S. PATENT DOCUMENTS

| 6,190,349 B1 * | 2/2001 | Ash ................ | A61M 25/0021 |
| | | | 604/27 |
| 8,206,354 B2 * | 6/2012 | Schon ............... | A61M 25/0029 |
| | | | 604/27 |
| 9,572,956 B2 * | 2/2017 | Nimkar ............. | A61M 25/0102 |
| 9,782,535 B2 * | 10/2017 | Anand ................ | A61M 1/285 |

(Continued)

FOREIGN PATENT DOCUMENTS

TR  201722797 U5 * 12/2017 ............ A61M 1/285

OTHER PUBLICATIONS

TR202722797U5 Google Patent machine translation accessed Jul. 11, 2024 (Year: 2024).*

*Primary Examiner* — Michael J Tsai
*Assistant Examiner* — Anthony Christopher Misistia
(74) *Attorney, Agent, or Firm* — Rutan & Tucker LLP

(57) ABSTRACT

Disclosed herein is a catheter defining a first lumen and a second lumen. A proximal portion of the catheter can be configured to separate along a longitudinal axis to allow a proximal portion of the first lumen to be trimmed to a different length than a proximal portion of the second lumen. The catheter can include a septum disposed laterally between the first lumen and the second lumen configured to facilitate separation of the first lumen from the second lumen. The septum can include grooves, perforations, and can be formed of different materials to facilitate separation. Further the septum can include a wire configured to facilitate separation of the first lumen from the second lumen. Separation and/or trimming of the lumens positions the subcutaneous access ports in a spaced apart relationship to differentiate between infusion and aspiration lumens of the catheter.

9 Claims, 5 Drawing Sheets

(56) References Cited

U.S. PATENT DOCUMENTS

| | | | |
|---|---|---|---|
| 2004/0254528 A1* | 12/2004 | Adams | A61M 25/0029 604/96.01 |
| 2006/0235458 A1* | 10/2006 | Belson | A61M 25/0032 606/191 |
| 2008/0154186 A1* | 6/2008 | Appling | A61M 25/0068 604/43 |
| 2009/0204052 A1* | 8/2009 | Nimkar | A61M 25/0009 604/523 |
| 2014/0163532 A1* | 6/2014 | Cornet | A61M 25/0071 604/319 |

* cited by examiner

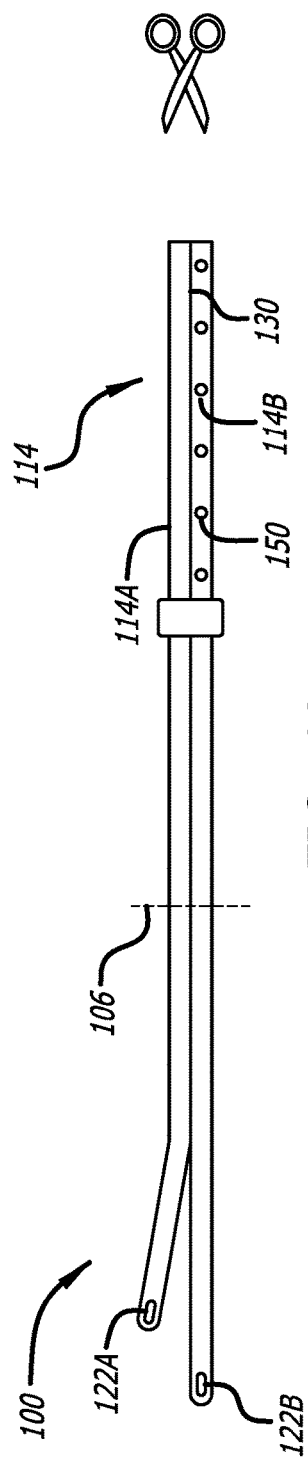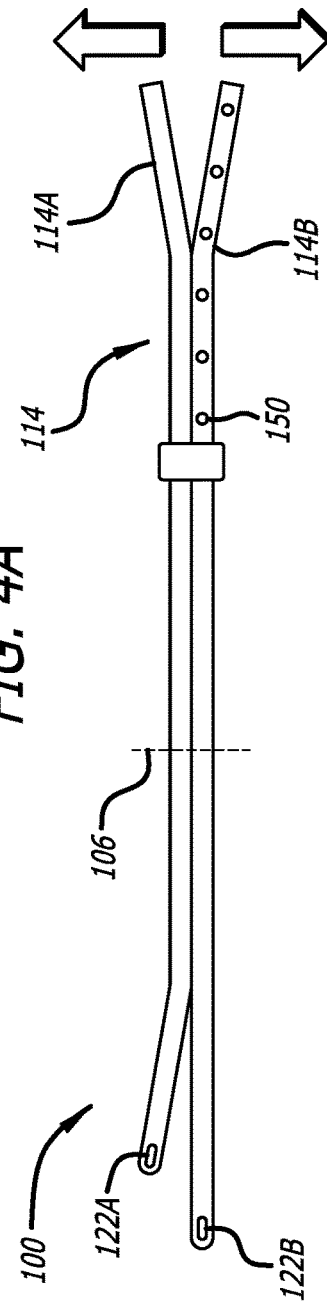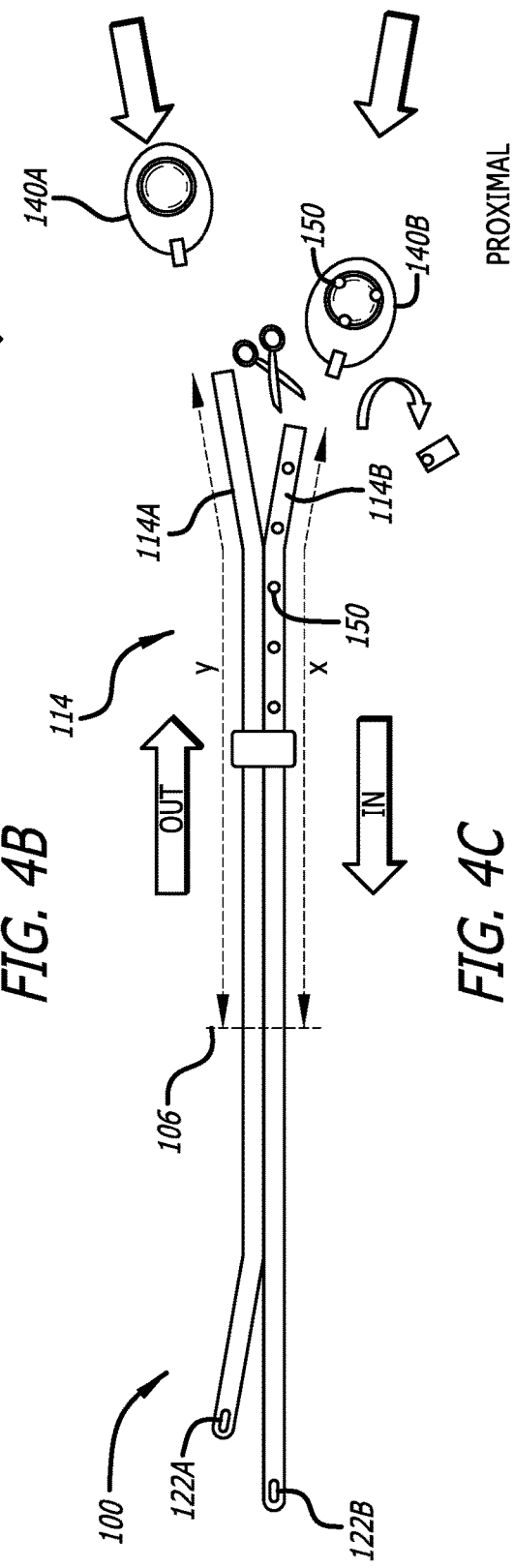

PROXIMALLY SEPERABLE CATHETERS AND ASSOCIATED METHODS

PRIORITY

This application claims the benefit of priority to U.S. Patent Application No. 63/086,995, filed Oct. 2, 2020, which is incorporated by reference in its entirety into this application.

SUMMARY

Embodiments disclosed herein are directed to proximally separable and trimmable catheters and associated methods thereof. Trimming each lumen to different lengths allows separate port devices to be coupled to each lumen and positioned subcutaneously. Subcutaneous dialysis access allows patients to swim, bathe or shower as normal, improving their overall quality of life. Trimming lumens to different lengths allows for differential positioning of the respective ports coupled thereto. The position of the ports allows for correct identification of dialysis lumens despite being disposed subcutaneously without requiring imaging.

Disclosed herein is a method of placing a catheter system including, providing a catheter including a body defining a first lumen and a second lumen, and including a septum disposed laterally between the first lumen and the second lumen, the first lumen and the second lumen defining an equivalent length from a longitudinal mid-point, creating a subcutaneous pocket in the patient, advancing a distal end of the first lumen to a first destination and a distal end of the second lumen to a second destination, separating a proximal portion of the first lumen from a proximal portion of the second lumen, trimming the first lumen to a first length, and trimming the second lumen to a second length, different from the first length, and coupling a first access device to the first lumen and a second access device to the second lumen, the first access device and the second access device disposed in a spaced apart relationship within the subcutaneous pocket.

In some embodiments, one of the first access device or the second access device is a low profile port. The first access device is disposed longitudinally proximally relative to the second access device. The septum includes a laser cut line, groove, score line, perforation, or line of weakness configured to allow the proximal portion of the first lumen to separate from the proximal portion of the second lumen. The catheter is formed of a first material, and a portion of the septum is formed of a second material different from the first material, the second material configured to allow the proximal portion of the first lumen to separate from the proximal portion of the second lumen. In some embodiments, the method further includes urging a wire transversely through the septum to separate the proximal portion of the first lumen from the proximal portion of the second lumen, the wire co-extruded with the septum to extend longitudinally therethrough.

Also disclosed is a catheter including, an elongate body defining a first lumen and a second lumen, and a septum disposed laterally between the first lumen and the second lumen and extending longitudinally, the septum extending transversely at least 30% of the transverse height of the elongate body, the septum is configured to allow a proximal portion of the first lumen to separate from a proximal portion of the second lumen.

In some embodiments, the proximal portion of the first lumen or the proximal portion of the second lumen is configured to be trimmable and coupled to a subcutaneous access device. The first lumen is configured to be trimmed to a different length from the second lumen such that a first subcutaneous access device is disposed longitudinally proximally relative to a second subcutaneous access device. The septum includes a laser cut line, groove, score line, perforation, or line of weakness configured to facilitate separation of the proximal portion of the first lumen from the proximal portion of the second lumen. The catheter is formed of a first material, and a portion of the septum is formed of a second material different from the first material and configured to facilitate separation of the proximal portion of the first lumen from the proximal portion of the second lumen. The first material includes a polymer, thermoplastic, or polyurethane, and the second material includes an elastomer or silicone rubber. The septum includes a wire extending longitudinally therethrough and configured to facilitate separation of the proximal portion of the first lumen from the proximal portion of the second lumen. The wire is formed of steel, titanium, or nitinol.

Also disclosed is a method for performing a dialysis procedure on a patient including, obtaining a catheter including a first lumen separated from a second lumen by a septum, the first lumen having a length equivalent to the second lumen, creating a subcutaneous pocket in the patient, measuring a first distance from a first location in the subcutaneous pocket to a first destination, measuring a second distance from a second location in the subcutaneous pocket to a second destination, separating the first lumen from the second lumen completely along the length, trimming the first lumen to match the first distance, and trimming the second lumen to match the second distance, introducing the first lumen and the second lumen into the patient, placing a distal end of the first lumen at the first destination and a distal end of the second lumen at the second destination, inserting a first access device and a second access device into the subcutaneous pocket, and connecting a proximal end of the first lumen to the first access device and a proximal end of the second lumen to the second access device.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 4A-4C illustrates an exemplary method of use for a catheter system, in accordance with embodiments disclosed herein.

DESCRIPTION

Figure 1:
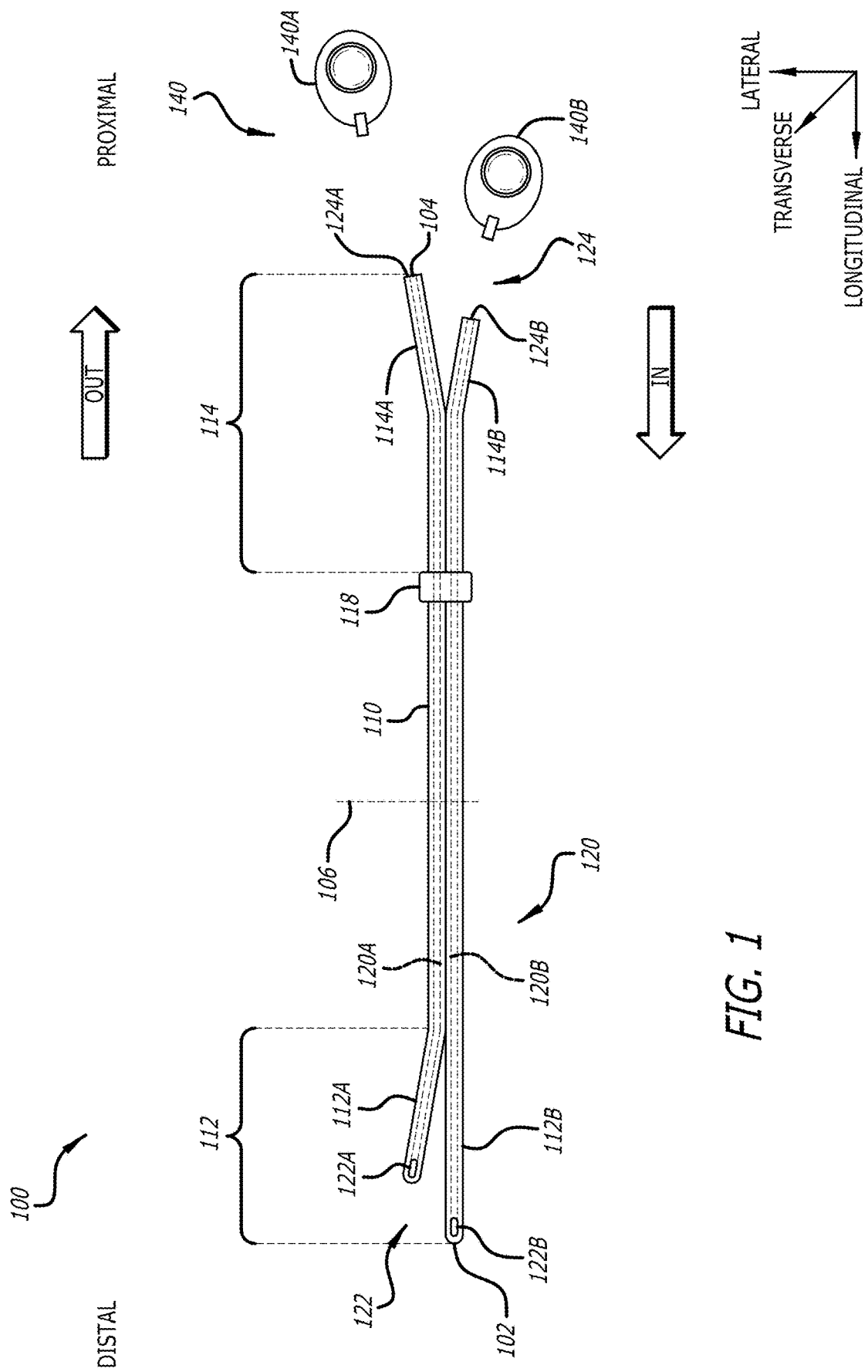
FIG. 1 illustrates an exemplary catheter system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

As shown in FIG. 1, and to assist in the description of embodiments described herein, a longitudinal axis extends substantially parallel to an axial length of the catheter. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

The present disclosure generally relates to proximally separable and trimmable catheter systems, and associated methods thereof. FIG. 1 shows an exemplary catheter system ("catheter") 100 including one or more subcutaneous access devices that can be coupled thereto. As shown, the catheter can be a central venous catheter (CVC), however this is not intended to be limiting and embodiments disclosed herein can be used with various exemplary catheters. Exemplary catheters can include peripherally inserted central catheters (PICC), midline catheters, peripherally inserted venous (PIV) catheters, dialysis catheters, multi-lumen catheters, or the like.

The catheter 100 can include an elongate body 110 extending from a distal end 102 to a proximal end 104, and can define one or more lumens 120. As shown, the catheter 100 defines a first lumen 120A and a second lumen 120B. However, it will be appreciated that catheters with greater or lesser numbers of lumens are also contemplated. Each lumen 120 extends from a proximal opening 124 disposed at a proximal end, to an eyelet 122 disposed adjacent the distal end 102. For example, the first lumen 120A provides fluid communication between a first eyelet 122A and a first proximal opening 124A. Similarly, the second lumen 120B provides fluid communication between a second eyelet 122B and a second proximal opening 124B. It will be appreciated that each lumen 120 can communicate with one or more eyelets 122 disposed either through a side wall of the elongate body 110 or at a distal end 102.

In an embodiment, the eyelet 122 can include a valve, slit valve, or the like, configured to control a fluid flow therethrough. In an embodiment, the valve can be configured to allow a fluid flow in a first direction but prevent fluid flow in a second opposite direction. In an embodiment, the valve can be configured to allow fluid flow in both directions, and open or close when a pressure differential is applied across the valve.

In an embodiment, each lumen 120 can be equal longitudinal lengths. In an embodiment, each lumen 120 can be of different longitudinal lengths. As shown, the second eyelet 122B can be disposed distally of the first eyelet 122A. However, in some embodiments the first eyelet 122A can be disposed distally of the second eyelet 122A. In an embodiment, the elongate body 110 can define both the first lumen 120A and the second lumen 120B. In an embodiment, a distal portion 112 of the elongate body 110 can form a split tip where a first distal portion 112A can define a distal portion of the first lumen 120A and include the first eyelet 122A. A second distal portion 112B can define a distal portion of the second lumen 120B and include the second eyelet 122B. In an embodiment, the first distal portion 112A and the second distal portion 112B can remain attached along an entire length thereof. In an embodiment, the first distal portion 112A and the second distal portion 112B can be attached with a soluble adhesive configured to dissolve when disposed within the vasculature 16 of the patient 14 and allow the first distal portion 112A to separate from the second distal portion 112B.

In an embodiment, the elongate body 110, or portion thereof, defining the first lumen 120A and the second lumen 120B can be formed as a single, integral structure. In an embodiment, the elongate body 110, or portion thereof, can be formed of a first structure defining the first lumen 120A and a second structure defining the second lumen 120B. The first structure and the second structure can then be attached to each other using welding, bonding, adhesive, or the like.

In an embodiment, the first distal portion 112A and the second distal portion 112B can releasably couple to each other along the longitudinal axis, using an adhesive, bonding, welding, or the like. In an embodiment, the first proximal portion 114A and the second proximal portion 114B can releasably couple to each other along the longitudinal axis, using an adhesive, bonding, welding, or the like. In an embodiment, the first distal portion 112A and the second distal portion 112B can releasably couple to each other using a tearable septum 130. In an embodiment, the first proximal portion 114A and the second proximal portion 114B can releasably couple to each other using a tearable septum 130, as described in more detail herein. In an embodiment, the catheter 100 can include a hub 118 disposed proximate a proximal end.

In an embodiment, a subcutaneous vascular access device, e.g. port 140, can be coupled to a proximal opening 124 to provide fluid communication between the subcutaneous access device 140 and the eyelet 122. For example, a first port 140A can be coupled to a first proximal opening 124A to provide fluid communication between the first port 140A and the first eyelet 122A. Similarly, a second port 140B can be coupled to a second proximal opening 124B to provide fluid communication between the second port 140B and the second eyelet 122B. Exemplary subcutaneous vascular access devices can include ports, dual reservoir ports, low profile ports, or the like. In an embodiment, the port 140 can be fluidly coupled to the catheter lumen 120 using a catheter lock, or similar mechanism to secure the port 140 thereto.

Figure 2:
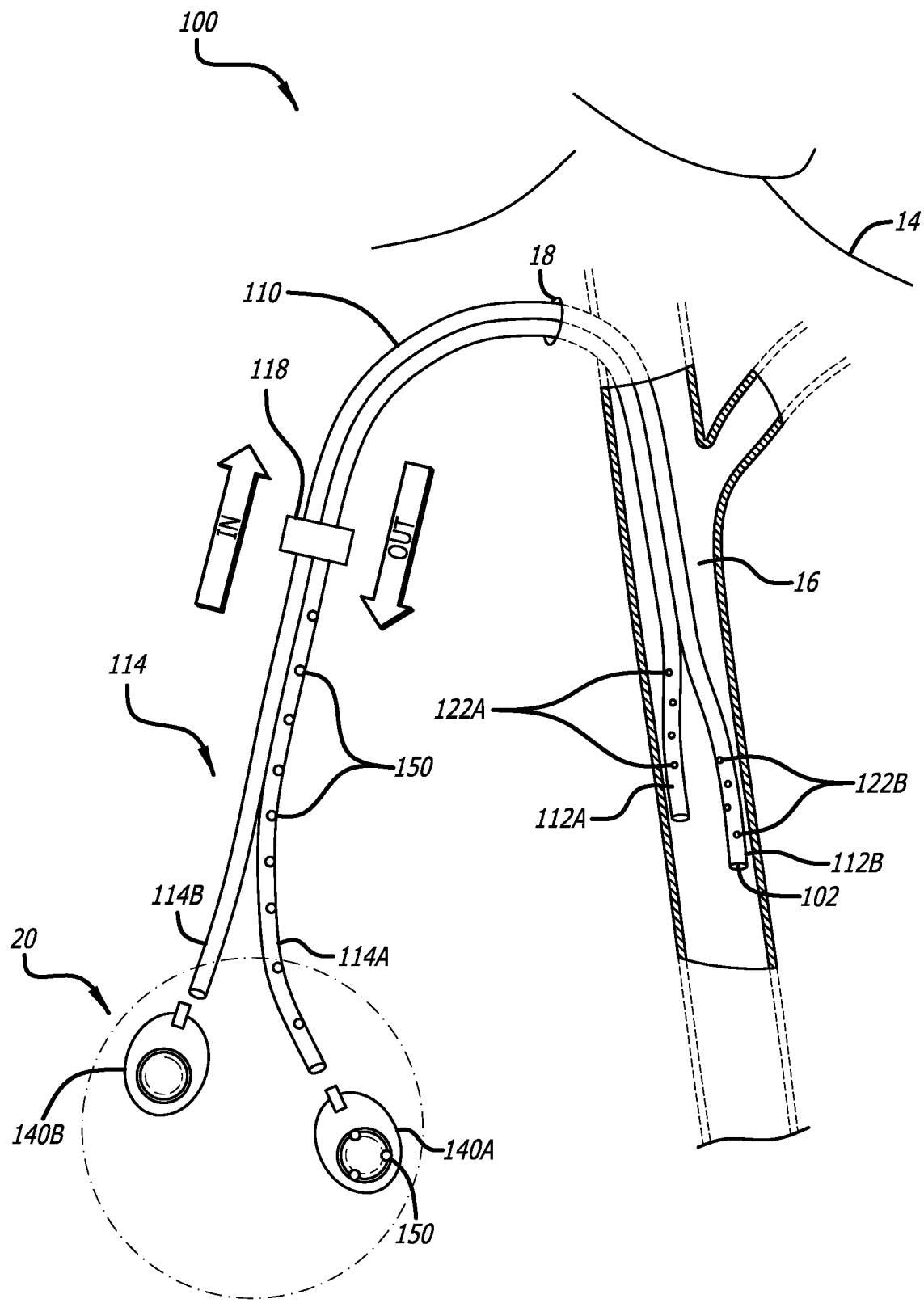
FIG. 2 illustrates the catheter system of FIG. 1 in an exemplary environment of use, in accordance with embodiments disclosed herein.

FIG. 2 shows the catheter system 100 of FIG. 1 in an exemplary environment of use within a patient 14. A distal portion 112 of the catheter 100 can be inserted through an insertion site 18 to access a vasculature 16 of the patient 14. The catheter 100 can be advanced until a distal end 102 is disposed proximate a target location e.g. a superior vena cava ("SVC"), or the like.

In an embodiment, the proximal portion 114 of the catheter 100 can extend from the insertion site 18 and be secured to a skin surface, or can extend subcutaneously to a subcutaneous access device 140, disposed at an access site 20. As will be appreciated, the distance between the target location, the insertion site 18, and the access site 20 can vary depending on the size of the patient, or the specific location of the insertion site 18 or the access site 20. As such the specific length of catheter required to extend from the target location to the insertion site 18 and to the access site 20 will vary. Advantageously, the proximal portion 114 of the catheter 100 can be trimmable to fit different catheter lengths. Further, the proximal portion 114 can be splittable to provide a first proximal portion 114A and a second proximal portion 114B that can each be trimmed to different lengths to suit the requirements of the procedure or position the ports 140. For example, a clinician may position the ports 140A, 140B in different positions within the access 20 to fit between different ribs. This can provide a lower profile and reduce scarring around the port 140, to improve the aesthetics of the subcutaneous port and quality of life for the patient.

In an embodiment, trimming the first proximal portion 114A to a different length from the second lumen 114B can position the ports 140 in a spaced apart relationship relative to the longitudinal axis of the catheter 100. Advantageously, this can indicate which lumen the port is coupled to. For example, the first eyelet(s) 122A communicating with the first lumen 112A are disposed proximally, or "upstream," relative to the second eyelet(s) 122B communicating with the second lumen 120B. During certain procedures, e.g. dialysis, it is important that blood be aspirated from the first lumen 120A and infused through the second lumen 120B. As such, to differentiate between the first port 140A and the second port 140B, the second proximal portion 114B can be trimmed to a shorter length than the first proximal portion 114A to indicate which of the ports 140 are coupled with the first lumen 120A or the second lumen 120B. In an embodiment, the first proximal portion 114A can be trimmed to a shorter length than the second proximal portion 114B.

Advantageously, with the subcutaneous ports 140 located at different longitudinal positions relative to the catheter 100, a clinician can quickly identify the "IN" lumen for infusion and the "OUT" lumen for aspiration by palpation, without requiring medical imaging, or similar additional equipment or procedures.

In an embodiment, one of the first proximal portion 114A or the second proximal portion 114B can include an identification feature 150. The identification feature 150 can be formed, or co-extruded, with the catheter body 110 to differentiate between the first lumen 120A or the second lumen 120B. Exemplary identification features can include protrusions, nubs, ridges, different color materials, printed alphanumeric symbols, combinations thereof, or the like. For example, the first proximal portion 114A can include a ridge extending along a longitudinal axis. Alternatively, or in addition, the first proximal portion 114A can include a plurality of protrusions disposed along a longitudinal axis. Advantageously, the protrusions, ridges, or the like, allow a clinician to palpate the proximal portions 114 of the catheter to differentiate between the first proximal portion 114A or the second proximal portion 114B.

In an embodiment, the identification feature can be a different colored material or printed alphanumeric symbol. Advantageously, when placing the catheter 100, a clinician can identify which lumen is for infusion or for aspiration and couple the correct port 140 thereto. This can be important where the port 140 to be coupled to the lumen includes different dimensions, configurations, or check valves configured for uni-directional flow depending on whether the port is to be used for infusion or aspiration. In an embodiment, the port can include an identification feature 150, e.g. bumps, rings, etc., as described herein.

Figure 3B:
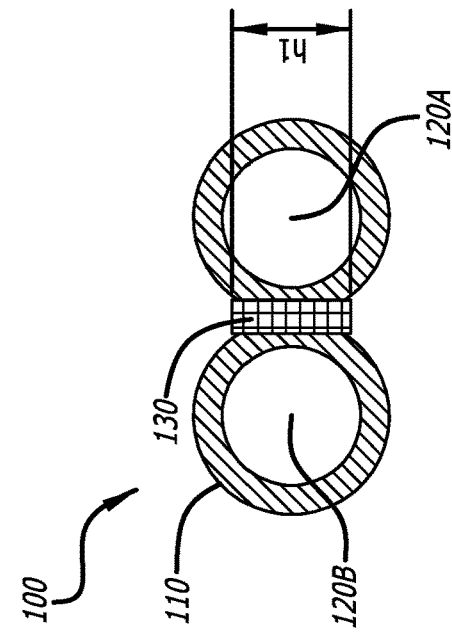
FIGS. 3A-3D illustrates cross-sectional views of a catheter system, in accordance with embodiments disclosed herein.
Figure 3D:
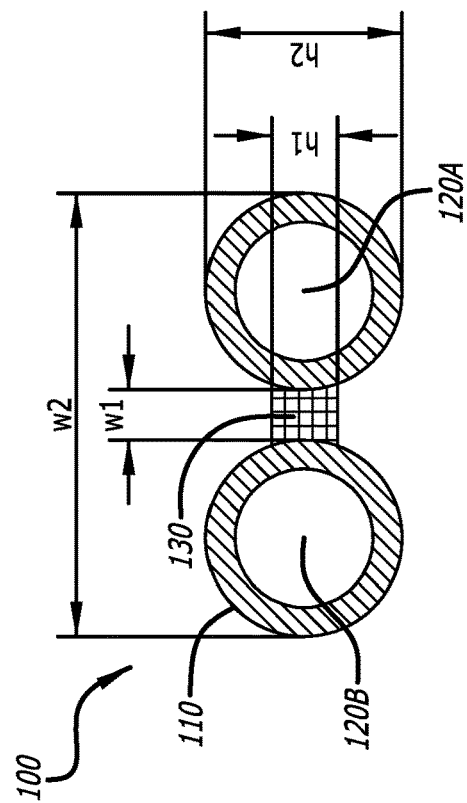
Figure 3A:
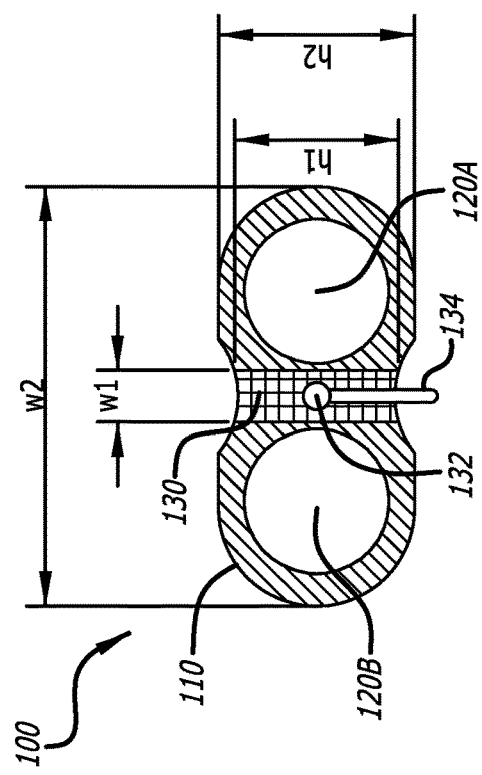
Figure 3C:
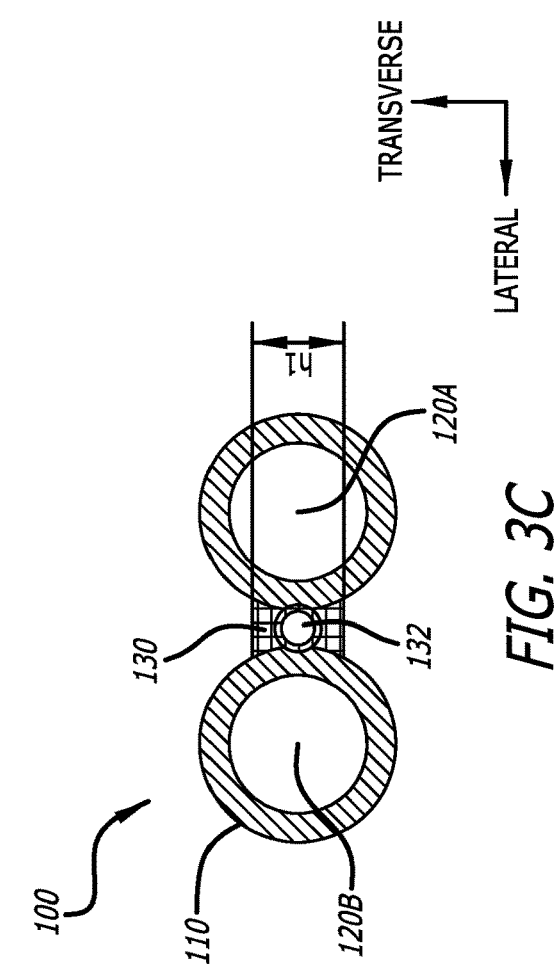

FIGS. 3A-3C show embodiments of cross-sectional views of the catheter 100. The cross-sectional views extend perpendicular to the longitudinal axis and can be disposed at any point along the catheter body 110, e.g. the distal portion 112, a mid-point 106, or the proximal portion 114.

As shown in FIG. 3A, in an embodiment, the catheter body 110 can be formed of a first material such as a plastic, polymer, thermoplastic, elastomer, rubber, silicone rubber, polyurethane, or the like. The catheter body 110 can define the first lumen 120A and the second lumen 120B as described herein. In an embodiment, the catheter body 110 can further include a tearable septum ("septum") 130 disposed laterally between the first lumen 120A and the second lumen 120B and extending longitudinally along a portion of the catheter body 110 between the distal end 102 and the proximal end 104. In an embodiment, the septum 130 extends from the distal end 102 to the proximal end 104. The tearable septum 130 can be configured to facilitate separation of the catheter body 110 along the longitudinal axis.

In an embodiment, a transverse height (h1) of the septum 130 can vary between 25% and 100% of the transverse height (h2) of the catheter body 110. In an embodiment, the transverse height (h1) of the septum 130 can be greater than 30% of the transverse height (h2) of the catheter body 110. In an embodiment, a lateral width (w1) of the septum 130 can vary between 9% and 20% of the lateral width (w2) of the catheter body 110. In an embodiment, the lateral width (w1) of the septum 130 can be greater than 12% of the lateral width (w2) of the catheter body 110. Advantageously, dimensions of the septum 130 can provide a secure attachment between first lumen 120A and the second lumen 120B of the elongate body 110.

In an embodiment, the septum 130, or portion thereof can be formed of the first material, i.e. the same material as the catheter body 110. In an embodiment, the septum 130 can include a laser cut line, groove, score line, perforation, or similar structural line of weakness configured to allow the first lumen 120A and the second lumen 120B to separate along the longitudinal axis. As used herein, a perforation can include a plurality of apertures extending transversely through the septum 130 from a top surface to a bottom surface.

In an embodiment, the septum 130, or portion thereof, can be formed of a second material, different from the first material, and configured to display different mechanical properties from the first material to facilitate separation therealong. Exemplary materials for the second material can include, plastic, polymer, thermoplastic, elastomer, rubber, silicone rubber, polyurethane, or the like. In an embodiment, the septum 130 can be formed of an adhesive configured to releasably attach a first portion of the body 110 to a second portion of the body 110. For example, a first distal portion 112A to a second distal portion 112B or a first proximal portion 114A to a second proximal portion 114B.

As shown in FIGS. 3A and 3C, in an embodiment, the septum 130 can include one or more wires 132 extending therethrough, parallel to the longitudinal axis. The wire 132 can be a single core or multi-core, straight or twisted wire. In an embodiment, the wire 132 can be formed of a metal, alloy, steel, titanium, nitinol, copper, plastic, polymer, composite, thermoplastic, or the like. In an embodiment, a portion of the wire 132, or a tab 134 coupled to the wire 132, can extend transversely through the septum 130 to extend from a surface of the catheter body 110. In use, a user can pull on the portion of the wire 132, or the tab 134, to pull the wire 132 transversely through the septum 130, cutting the septum 130 and facilitating separation of the septum 130 along the longitudinal axis. Optionally, a clinician can snip a portion of the septum 130 to expose a portion of the wire 132 disposed therein. The user can then grasp the wire 132 to pull the wire 132 through the septum 130 and separate the septum 130, as described herein.

In an exemplary method of use, as shown in FIGS. 2 and 4A-4C, a catheter system 100 is provided including a proximally trimmable and separable portion 114, as described herein. The clinician can advance a distal portion 112 through an insertion site 18 to a target location within a vasculature 16 of the patient 14. A proximal portion 114 can extend from the insertion site 18, and optionally be secured to a skin surface. In an embodiment, the proximal portion 114 can extend subcutaneously to an access site 20. The access site 20 can include one or more tissue pockets configured to receive a subcutaneous vascular access device, such as a low profile port ("port") 140, or the like.

As shown in FIG. 4A, the first proximal portion 114A and the second proximal portion 114B can remain attached to each other along an entire length of the proximal portion 114. Advantageously, this can facilitate urging the proximal portion from the insertion site 18, subcutaneously to the access site 20. Once the proximal portion 114 has been positioned with the access site 20, e.g. tunneled subcutaneously to the access site 20, the clinician can separate the first proximal portion 114A from the second proximal portion 114B.

As shown in FIGS. 4A-4B the clinician can then urge the first proximal portion 114A away from the second proximal portion 114B, causing the catheter body 110 to separate along the septum 130. In an embodiment, the clinician can cut a portion of the septum 130 along the longitudinal axis to facilitate separation of the first proximal portion 114A and the second proximal portion 114B. In an embodiment, the clinician can pull a portion of the wire 132, extending longitudinally through the septum 130 to facilitate separation of the septum 130. In an embodiment, the clinician can trim a longitudinal length of the proximal portion 114 prior to separating the first portion 114A from the second portion 114B.

As shown in FIG. 4C, with the first proximal portion 114A separated from the second proximal portion 114B, the clinician can then trim one of the first proximal portion 114A or the second proximal portion 114B to a desired length. In an embodiment, the first proximal portion 114A and the second proximal portion 114B can be trimmed to the same length (e.g. distance x) relative to a longitudinal mid-point 106 of the catheter 110. In an embodiment, the first proximal portion 114A and the second proximal portion 114B can be trimmed to different lengths. For example, the first portion 114A can be trimmed to a length (y) relative to a mid-point 106 and the second portion 114B can be trimmed to a length (x) relative to a mid-point 106. Once trimmed, a port 140 can then be coupled with the proximal opening 124. For example, a first port 140A can be coupled to a first proximal opening 124A to provide fluid communication between the first port 140A and the first eyelet 122A. Similarly, a second port 140B can be coupled to a second proximal opening 124B to provide fluid communication between the second port 140B and the second eyelet 122B. In an embodiment, the port 140 can be coupled to the proximal opening 124 using a catheter lock or similar mechanism to secure the port 140 thereto.

In an embodiment, the second proximal portion 114B can be trimmed to a shorter length relative to the first proximal portion 114A. As such, the second port 140B can be disposed distally of the first port 140A. Further, since the first proximal portion 114A is separated from the second proximal portion 114B, the first port 140A can be disposed in a laterally spaced apart relationship relative to the second port 140B.

Advantageously, the clinician can choose the length of longitudinal separation or the length of longitudinal trimming, after the catheter distal end 102 is positioned correctly. The clinician can trim the proximal portions 114A, 114B, to choose the preferred lateral and longitudinal positions of the first and second proximal openings 124A, 124B and the first and second ports 140A, 140B coupled thereto. The clinician can adjust the lateral and longitudinal positions of the ports 140 to fit the position of the tissue pocket(s) at the access site 20, or to suit the rib structure of the individual patient. Further, the clinician can adjust the lateral and longitudinal positions of the ports 140 to differentiate the lumens 120A, 120B, indicating which lumen is for infusion and which lumen is for aspiration.

For example, as shown, the first eyelet 122A is disposed proximally, and therefore upstream, of the second eyelet 122B. As such, an "OUT" flow of blood to be aspirated can be drawn from the first lumen 120A and an "IN" flow of blood to be infused can be returned to the vasculature through the second lumen 120B, since the second eyelet 122B is positioned downstream of the first eyelet 122A within the vasculature 16.

In an embodiment, a second proximal portion 114B can be trimmed shorter than the first proximal portion 114A such that the first port 140A is disposed proximally of the second port 140B, mirroring the relative positions of the first eyelet 122A and the second eyelet 122B, indicating which of the lumens 120 are for aspiration or infusion. Similarly, separating the first proximal portion 114A from the second proximal portion 114B allows for the first port 140A to be laterally spaced apart relative to the second port 140B to facilitate identification of the different ports 140 by palpation when disposed subcutaneously. In an embodiment, the first proximal portion 114A can be trimmed to a shorter length than the second proximal portion 114B indicating that the overall length of the first lumen 120A is shorter than the overall length of the second lumen 120B and to identify which lumen is for infusion and which lumen is form aspiration.

In an embodiment, one of the first proximal portion 114A or the second proximal portion 114B can include an identification feature 150 to indicate to a user which of the first proximal portion 114A or the second proximal portion 114B is for infusion and which is for aspiration. In an embodiment, one of the ports 140A, 140B can include an identification feature to differentiate between infusion or aspiration lumens. In an embodiment, the first port 140A and the second port 140B can include a one-way check valve to prevent incorrect flow direction. For example a first check valve in the first port 140A can allow a fluid flow in a first direction and a second check valve in the second port 140B can allow a fluid flow in a second direction, opposite the first direction. The ports 140A, 140B can then be sutured in place within the access site 20 to mitigate subcutaneous travel.

Figure 5A:
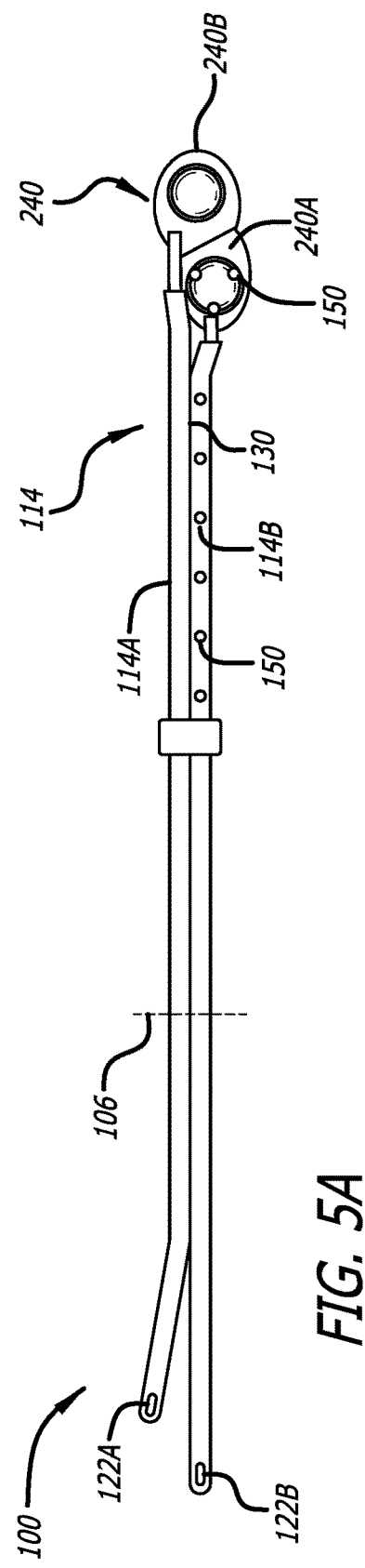
FIGS. 5A-5B illustrates an exemplary method of use for a catheter system, in accordance with embodiments disclosed herein.
Figure 5B:
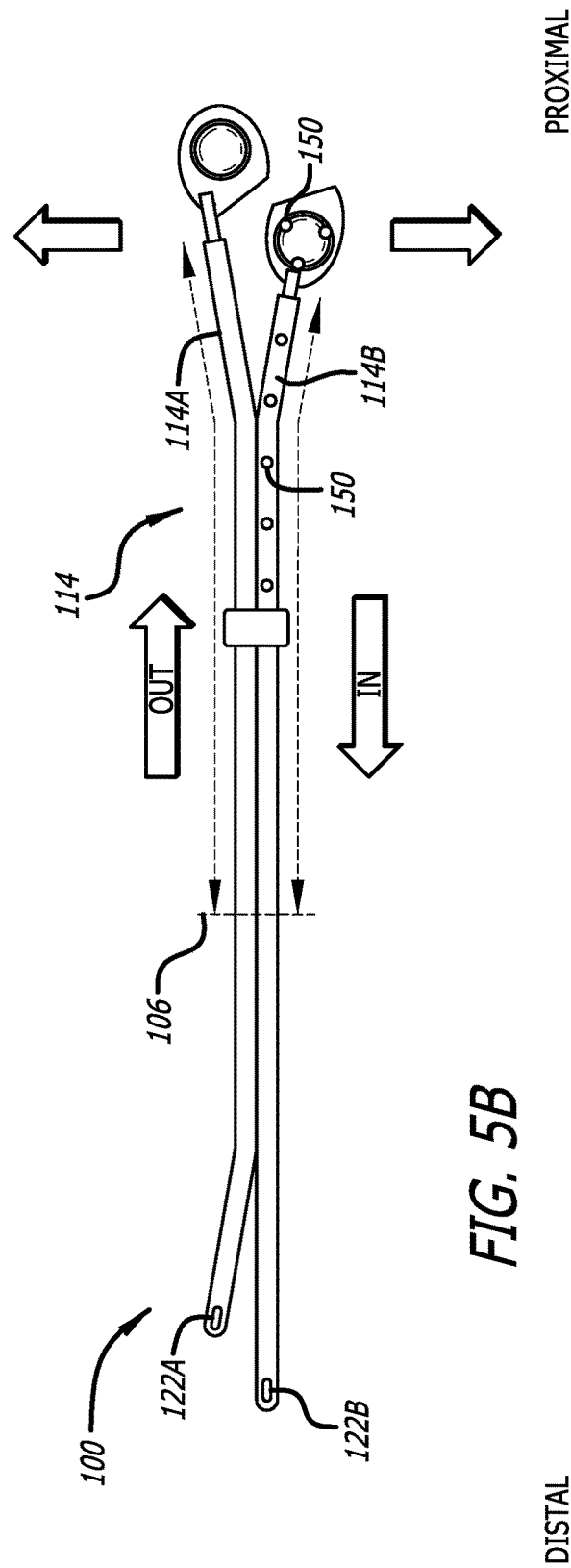

As shown in FIGS. 5A-5B, in an embodiment, the catheter system 100 can be provided with the first proximal portion 114A and the second proximal portion 114B attached along substantially the entire length of the proximal portion 114. A first port 240A and a second port 240B can be pre-attached to the first proximal portion 114A and the second proximal portion 114B respectively. The ports 240A, 240B can be releasably coupled to each other to form a continuous outer profile. In an embodiment, the outer profile can be configured to facilitate subcutaneous tunneling of the ports 240A, 240B as they remain coupled together.

Once positioned proximate the access site 20, the clinician can then urge the ports 240 apart to separate the first port 240A from the second port 240B and separate the first proximal portion 114A from the second proximal portion 114B. In an embodiment, one of the first proximal portion 114A or the second proximal portion 114B can be longer to position the first port 240A and the second port 240B at different longitudinal positions. Advantageously, the ports 140A, 140B can be "nested" next to each other and reduce an overall width of the ports 140A, 140B, which can facilitate tunneling from the insertion site 18 to the access site 20. In an embodiment the first port 240A can be releasably coupled with the second port 240B with an adhesive, frangible portion, or septum 130, as described herein. In an embodiment, the first port 240A can be releasably coupled with the second port 240B with a clip, lug, interference fit, or similar selectably releasable mechanism, to facilitate tunneling from the insertion site 18 to the access site 20.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of placing a catheter system, comprising:
providing a catheter including a body formed of a first material and defining a first lumen and a second lumen, and including a septum formed of a second material and disposed laterally between the first lumen and the second lumen, the first lumen and the second lumen defining an equivalent length from a longitudinal midpoint;
creating a subcutaneous pocket in a patient;
advancing a distal end of the first lumen to a first destination and a distal end of the second lumen to a second destination;
separating a proximal portion of the first lumen from a proximal portion of the second lumen by urging a wire, formed of a third material, transversely through the septum to separate the proximal portion of the first lumen from the proximal portion of the second lumen;
trimming the first lumen to a first length, and trimming the second lumen to a second length, different from the first length; and
coupling a first access device to the first lumen and a second access device to the second lumen, the first access device and the second access device disposed in a spaced apart relationship within the subcutaneous pocket.

2. The method according to claim 1, wherein one of the first access device or the second access device is a low profile port.

3. The method according to claim 1, wherein the first access device is disposed longitudinally proximally relative to the second access device.

4. The method according to claim 1, wherein the septum includes a laser cut line, groove, score line, perforation, or line of weakness configured to allow the proximal portion of the first lumen to separate from the proximal portion of the second lumen.

5. The method according to claim 1, wherein the first material of the catheter is different from the second material of the septum, the second material configured to allow the proximal portion of the first lumen to separate from the proximal portion of the second lumen.

6. The method according to claim 1, wherein the wire is co-extruded with the septum to extend longitudinally therethrough.

7. The method according to claim 1, wherein the wire is formed of a straight, single core wire.

8. The method according to claim 1, wherein the wire is formed of as a multi-core, twisted wire.

9. The method according to claim 1, wherein the third material is a metal, alloy, steel, titanium, nitinol, copper, or composite.

* * * * *